(12) United States Patent
Lane et al.

(10) Patent No.: US 8,443,662 B2
(45) Date of Patent: May 21, 2013

(54) GEO-LOCATION SYSTEMS AND METHODS BASED ON ATMOSPHERIC PRESSURE MEASUREMENT

(75) Inventors: Benjamin F. Lane, Grafton, MA (US); Catherine L. Slesnick, Somerville, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 146 days.

(21) Appl. No.: 13/016,055

(22) Filed: Jan. 28, 2011

(65) Prior Publication Data

US 2012/0192622 A1 Aug. 2, 2012

(51) Int. Cl.
*G01C 21/00* (2006.01)

(52) U.S. Cl.
USPC ........................................................ 73/178 R

(58) Field of Classification Search
None
See application file for complete search history.

(56) References Cited

U.S. PATENT DOCUMENTS

| | | | |
|---|---|---|---|
| 5,675,081 A * | 10/1997 | Solheim et al. | 73/170.28 |
| 6,067,852 A * | 5/2000 | Alber et al. | 73/178 R |
| 7,224,273 B2 | 5/2007 | Forster | |
| 7,659,816 B2 | 2/2010 | Wandel | |
| 8,018,383 B1 * | 9/2011 | Schantz et al. | 342/453 |
| 2004/0186635 A1 * | 9/2004 | Manfred | 701/4 |
| 2005/0068177 A1 | 3/2005 | Chun et al. | |
| 2006/0214789 A1 | 9/2006 | Posamentier et al. | |
| 2008/0042844 A1 | 2/2008 | Christopher | |
| 2008/0159547 A1 | 7/2008 | Schuler et al. | |
| 2010/0103825 A1 * | 4/2010 | Taaghol et al. | 370/245 |
| 2012/0182180 A1 * | 7/2012 | Wolf et al. | 342/357.29 |

\* cited by examiner

*Primary Examiner* — Andre Allen
(74) *Attorney, Agent, or Firm* — Goodwin Procter LLP

(57) ABSTRACT

System and method for geo-location of a device (such as a tag) using barometric pressure readings taken in the vicinity of the device and correlated to datasets of barometric pressure that have pressure gradients over time and space. The readings taken in the vicinity of the device may be correlated to the datasets using an iterative Bayesian approach to determine a geo-location of the device with a high degree of confidence.

42 Claims, 8 Drawing Sheets

GEO-LOCATION SYSTEMS AND METHODS BASED ON ATMOSPHERIC PRESSURE MEASUREMENT

FIELD OF THE INVENTION

In various embodiments, the present invention relates to geo-location, positioning, and/or mapping techniques, and more specifically to geo-location systems and methods based on atmospheric pressure measurement.

BACKGROUND OF THE INVENTION

The general problem of geo-location or navigation has been studied for centuries. Prior methods include various forms of dead reckoning, inertial navigation, celestial navigation, and radio-navigation, which are too numerous to list here.

The disadvantages of prior methods for geo-location generally are two-fold: either the methods require access to some form of external aiding signal (man-made or natural, such as global positioning system (GPS) signals or a view of the stars), or they do not provide sufficient accuracy in a small, low-power package. For example, inertial navigation systems are typically large and require significant amounts of power, and they also tend to produce results that drift over time.

Accordingly, there is a need for improved systems and methods that can determine the geographic location of an object without assistance from external radio signals.

SUMMARY OF THE INVENTION

In various embodiments, the present invention relates to geo-location systems and methods based on atmospheric pressure measurement.

One object of the invention is to determine the geo-location of a small sensor (sometimes referred to as a "tag") without recourse to GPS or other externally provided navigational signals. The tag works by recording atmospheric pressure variations. After the tag has been recovered, this record may then be correlated with atmospheric models and thereby the location history of the tag can be determined. The geo-location techniques according to the present invention require only a very small sensor package in the object to be located, consisting essentially of a simple pressure (and optional temperature) recorder. The bulk of the navigational problem is moved to the post-processing stage once the tag has been recovered. The only external information required by the invention is the atmospheric pressure, which will generally be available, even in situations where other navigational signals are not.

Although barometric pressure sensors have been used as aiding sensors to inertial navigational units, in such an application the sensor is merely used to sense changes in altitude, not to provide a true geo-location measurement. The novel approach described herein correlates the pressure data against external databases and/or models to yield location independent of any inertial navigation.

In one aspect, embodiments of the invention feature a method for determining a geo-location of an object. The method involves comparing a plurality of ambient atmospheric pressure measurements obtained for an object against a gridded atmospheric model; and based at least in part on the comparison, determining a geo-location of the object. In various embodiments the geo-location of the object is determined without using an externally provided navigation signal. Moreover, the geo-location of the object may be determined without using a global positioning system signal.

In other embodiments of this aspect of the invention the method further involves using a pressure sensor, associated with the object, to obtain the plurality of ambient atmospheric pressure measurements for the object. In various embodiments the plurality of ambient atmospheric pressure measurements is stored in computer memory. Moreover, the ambient atmospheric pressure may be measured and stored in the computer memory as a function of time.

In other embodiments of this aspect of the invention the method further involves compensating for environmentally-induced errors in the pressure measurements. In various embodiments the humidity in a vicinity of the object is measured to compensate for the environmentally-induced errors. Further, the temperature in a vicinity of the object may be measured to compensate for the environmentally-induced errors. Further still, the parameters measured to compensate for the environmentally-induced errors may be stored in a computer memory. Moreover, the parameter may be measured and stored in the computer memory as a function of time.

In other embodiments of this aspect of the invention the method further involves determining periods of time during which the object is being moved.

In other embodiments of this aspect of the invention, the plurality of ambient atmospheric pressure measurements are obtained while the object is static. Moreover, the comparison may include determining a geo-location at which a variance between the plurality of ambient atmospheric pressure measurements and corresponding pressure data from the gridded atmospheric model may be minimized.

In other embodiments of this aspect of the invention, the plurality of ambient atmospheric pressure measurements are obtained while the object is in motion. Moreover, at least one of an initial or a final location of the object may be provided. Further, a maximum speed experienced by the object may be provided. And further still, the comparison may comprise performing an iterative Bayesian procedure.

In other embodiments of this aspect of the invention, the gridded atmospheric model is a model employed by a meteorological forecasting agency.

For example, the gridded atmospheric model may be provided by the Rapid Update Cycle Surface Assimilation System maintained by the National Oceanic and Atmospheric Association, or by the Modern Era Retrospective—Analysis for Research and Applications maintained by the National Aeronautics and Space Administration.

In other embodiments of this aspect of the invention, the object is attached, during the plurality of ambient atmospheric pressure measurements, to at least one of a shipping container, a manufacturing supply, or an individual.

In another aspect, embodiments of the invention feature a system for determining a geo-location of an object based at least in part on a plurality of ambient atmospheric pressure measurements obtained for the object. The system includes an analysis module for comparing the ambient atmospheric pressure measurements against a gridded atmospheric model and for determining, based at least in part on the comparison, the geo-location of the object.

In various embodiments of this aspect of the invention, the analysis module determines the geo-location of the object without using an externally provided navigation signal. Moreover, the analysis module determines the geo-location of the object without using a global positioning system signal.

In various embodiments of this aspect of the invention, the system further includes a pressure sensor, associated with the object, for measuring the ambient atmospheric pressure. The system may further include a computer memory, associated with the object, for storing the plurality of ambient atmospheric pressure measurements. Moreover, the pressure sensor may measure the ambient atmospheric pressure as a function of time and the computer memory may store the ambient atmospheric pressure measurements as a function of time. In yet another embodiment, the pressure sensor may obtain the plurality of ambient atmospheric pressure measurements while the object is static. Moreover, the analysis module may determine a geo-location at which a variance between the plurality of ambient atmospheric pressure measurements and corresponding pressure data from the gridded atmospheric model is minimized.

In another embodiment, the pressure sensor obtains the plurality of ambient atmospheric pressure measurements while the object is in motion. Moreover, the system may include an input module, in operative communication with the analysis module, for receiving at least one of an initial or a final location of the object. Further still, the system may include an input module, in operative communication with the analysis module, for receiving a maximum speed experienced by the object. Moreover, the analysis module may execute an iterative Bayesian procedure.

In various embodiments of this aspect of the invention, the system further includes an auxiliary sensor, associated with the object, to compensate for environmentally-induced errors in the pressure measurements. Moreover, the auxiliary sensor may include a temperature sensor for measuring a temperature in a vicinity of the object. The auxiliary sensor may also include a humidity sensor for measuring a humidity in a vicinity of the object. The system may also include a computer memory, associated with the object, for storing a parameter measured by the auxiliary sensor. Moreover, the auxiliary sensor may measure the parameter as a function of time and the computer memory may store the measured parameter as a function of time.

In other embodiments of this aspect of the invention, the system furthers include at least one of a vibration or an acceleration sensor, associated with the object, for determining periods of time during which the object is being moved.

In other embodiments of this aspect of the invention, the system may further include a gridded atmospheric model. Moreover, the gridded atmospheric model may be a model employed by a meteorological forecasting agency. For example, the gridded atmospheric model may also be provided by the Rapid Update Cycle Surface Assimilation System maintained by the National Oceanic and Atmospheric Association, or by the Modern Era Retrospective—Analysis for Research and Applications maintained by the National Aeronautics and Space Administration.

Other embodiments of the invention involving steps and configurations not described above would also be apparent to those of ordinary skill in the art from the detailed description provided herein.

BRIEF DESCRIPTION OF DRAWINGS

The advantages of the invention may be better understood by referring to the following drawings taken in conjunction with the accompanying description.

In the drawings, like reference characters generally refer to corresponding parts throughout the different views. The drawings are not necessarily to scale, emphasis instead being placed on illustrating the principles and concepts of the invention.

DETAILED DESCRIPTION OF THE INVENTION

Overview

In brief overview, embodiments of the present invention provide the capability to geo-locate a geo-location device (such as a tag) using barometric pressure. Tracking a device according to ambient atmospheric pressure of a device may be accomplished due to significant pressure gradients over time and space. Embodiments use databases of historical pressure measurements over time and over fixed Earth-based grids and correlate those databases to pressure measurement read by a device with a pressure sensor to track the device.

The ambient pressure is low bandwidth data, sufficient to localize a geo-location device within kilometers or closer to its actual location. This approach enables geo-location in RF-denied environments, requires minimal power consumption, minimal memory, and minimal data volume, and does not require an antenna. The geo-location techniques described herein work without requiring reception of external radio-navigational signals such as GPS. In addition, due to its efficiency, the sensor may be very small.

Exemplary embodiments of the invention include a small autonomous tracking device that may be covert and RF-denied. The sensor may be a barometer which measures atmospheric pressure as the device moves along an unknown path over time.

DESCRIPTION OF EXEMPLARY EMBODIMENTS

Figure 1:
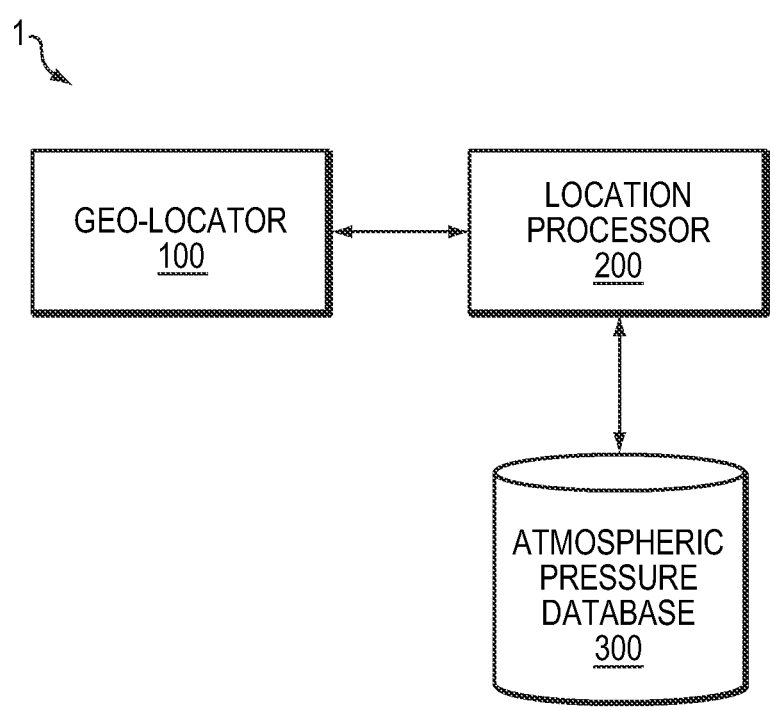
FIG. 1 is a block diagram of a system for determining the geo-location of a device according to an exemplary embodiment of the invention.

FIG. 1 illustrates a system according to an exemplary embodiment of the invention. The System 1 includes a Geo-locator 100, a Location Processor 200, and an Atmospheric Pressure Database 300. In one embodiment, the System 1 may be a single device. In another embodiment, the Location Processor 200 and Atmospheric Pressure Database 300 are a single device, and the Geo Locator 100 is a separate device, capable of being communicably connected to the rest of the System 1. In another embodiment, the Geo-locator 100 and the Location Processor 200 are a single device, and the Atmospheric Pressure Database 300 is a separate unit, capable of being communicably connected to the rest of System 1. In yet another embodiment, the Geo-locator 100, Location Processor 200 and the Atmospheric Pressure Database 300 are separate units.

In embodiments of the invention, the Atmospheric Pressure Database 300 utilizes publicly available data sets of gridded atmospheric pressure data, and may in fact be a publicly available database. Examples of sources of publicly available databases include the Rapid Update Cycle Surface Assimilation System maintained by the National Oceanic and Atmospheric Association, the Modern Era Retrospective—Analysis for Research and Applications maintained by the National Aeronautics and Space Administration, and datasets maintained by the European Centre for Medium-Range Weather Forecasts.

The present invention may use a custom infrastructure and rely on the publicly available data. The Location Processor 200 may use a number of data-correlation algorithms (examples of which are described in Appendix A) to match atmospheric pressure measurements with known data sets or models of atmospheric pressure. By implementing more sophisticated algorithms or accuracy-enhancement methods, the geo-location techniques according to the present invention may be further improved in all areas such as minimizing the amount of data required for a position fix, maximizing the position accuracy, and extending the geo-location capability to moving targets on land.

Figure 2:
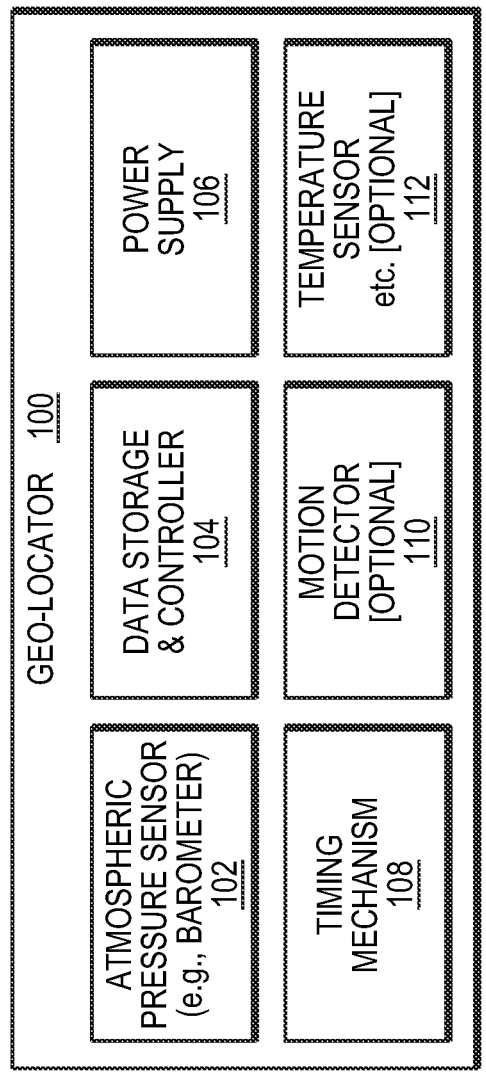
FIG. 2 is a block diagram of a Geo-locator device according to an exemplary embodiment of the invention.

FIG. 2 illustrates a Geo-locator 100 according to an exemplary embodiment of the invention. The Geo-locator 100 includes an Atmospheric Pressure Sensor 102, Data Storage and Controller 104, a Power Supply 106 and a Timing Mechanism 108. In some embodiments, the Geo-locator 100 also includes a Motion Detector 110 and a Temperature Sensor 112. The Atmospheric Pressure Sensor 102 and Data Storage and Controller 104 log measurements of ambient pressure.

The storage capacity of the Data Storage and Controller 104 may vary according to the period of time during which pressure measurement data is collected. Typically, the storage capacity will be at least capable of storing a few Kilobytes of data.

The Timing Mechanism 108 may be a clock (e.g., a digital circuit, an oscillating crystal, etc.). The accuracy of the Timing Mechanism 108 will typically be a fraction of the sample time, for example when utilizing once-per-minute sampling a clock accuracy of tens of seconds per minute is typically sufficient.

The Atmospheric Pressure Sensor 102 typically has a measurement precision in the range of a few Pascal, with an accuracy of ~1%. In one embodiment, the Geo-locator 100 further includes one or more auxiliary sensors such as temperature sensors (for temperature-compensation) or humidity sensors (for sea-level reduction and altitude compensation) which provide additional environmental data for improving the accuracy of measurements collected by the Atmospheric Pressure Sensor 102. Atmospheric pressure measurement data collected by the Atmospheric Pressure Sensor 102 may be adjusted based on humidity data and temperature data according to known correlations between the rate of air pressure change as a function of air temperature and humidity.

In one embodiment the Geo-locator 100 is a sensor tag where the Atmospheric Pressure Sensor 102 and the Data Storage and Controller 104 are a small pressure and temperature recorder based on microelectromechanical systems (MEMS) technology. In one embodiment the Timing Mechanism 108 enables the Atmospheric Pressure Sensor 102 to detect and record the ambient atmospheric pressure as a function of time, for example, at a precision comparable to commercially available systems (i.e. 50-100 Pa). For optimal performance the cadence should be sufficient to resolve small-scale atmospheric fluctuations (e.g., once/min), although adequate results may be achieved with less fine attenuation. In one embodiment, a vibration or acceleration sensor may be included in or with the Geo-locator 100. A vibration sensor may be used to determine periods of time that the Geo-locator 100 moves or periods of time that the Geo-locator 100 is static. In another embodiment, the acceleration sensor is an accelerometer that measures changes in tilt of the Geo-locator 100; the tilting or pitching of the Geo-Locator 100 may be interpreted to indicate movement by the Geo-locator 100. In one embodiment, atmospheric pressure data collected while the Geo-locator 100 moves is discarded before applying a location algorithm that assumes the Geo-locator 100 is static.

Figure 3:
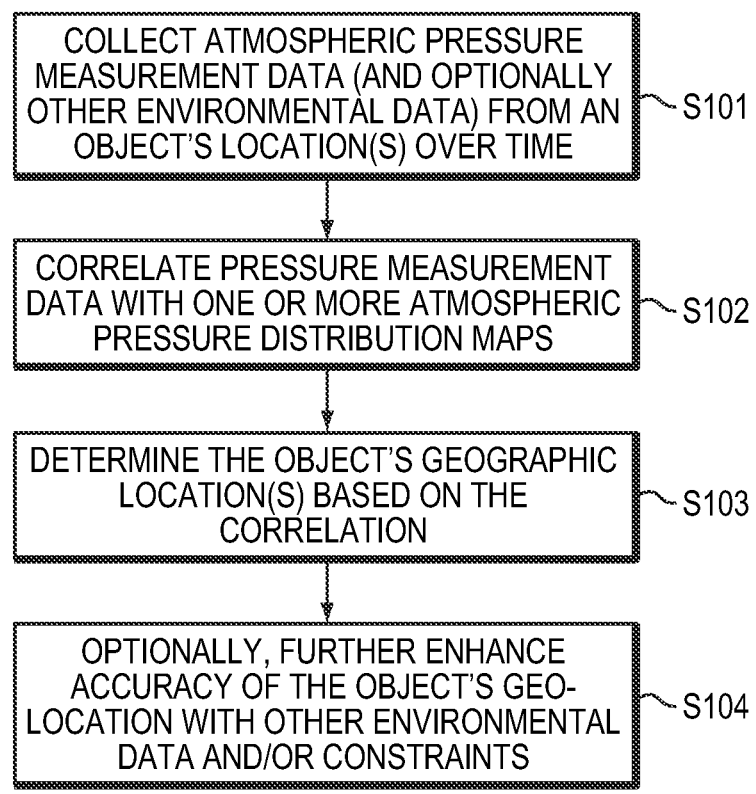
FIG. 3 is a flow-chart illustrating a method for determining the geo-location of a device according to an exemplary embodiment of the invention.
Figure 6:
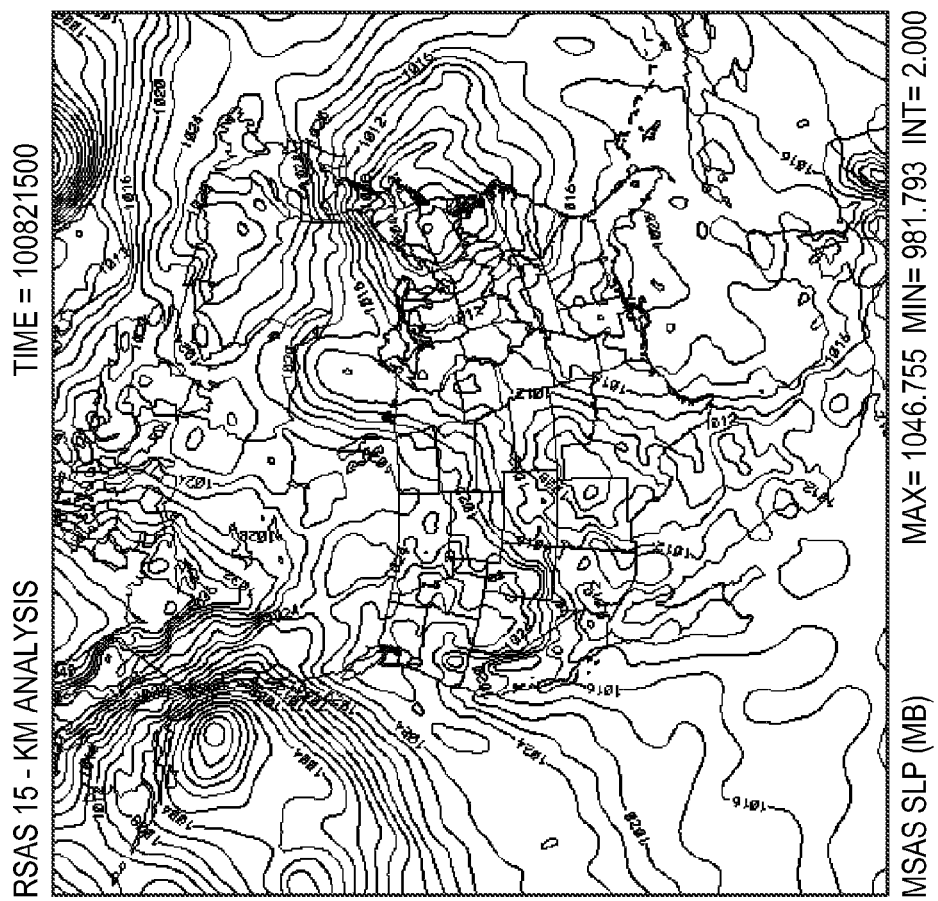
FIG. 6 is an example of a pressure grid provided by the Rapid Update Cycle Surface Assimilation System.

FIG. 3 illustrates an exemplary operation of the System 1, with reference to FIGS. 1 and 2. First, the Atmospheric Pressure Sensor 102 collects ambient atmospheric pressure measurement data over a period of time (also referred to herein as the "pressure history"), storing the collected data in the Data Storage and Controller 104 (Step S101). In one exemplary embodiment, the time period is a setting in the Geo-locator 100. In one embodiment, the Atmospheric Pressure Sensor 102 ALSO collects other environmental data, for example temperature, altitude, type of terrain, humidity, wind speed, light, weather data, etc., to improve the accuracy of the location determination. Upon receiving the ambient atmospheric pressure measurement data, the Location Processor 200 correlates the measurement data with one or more atmospheric pressure distribution maps (also referred to herein as "pressure grids") stored in the Atmospheric Pressure Database 300 (Step S102). Based on the correlations, the Location Processor 200 determines the location or locations (also referred to herein as the "position history") of the Geo-locator 100 over the period of time (Step S103). Optionally, the Location Processor 200 enhances the accuracy of the location results determined in the previous step using the measured environmental data and other constraints (Step S104). In Steps S102 and S103, the position history of the Geo-locator 100 may be recovered by comparing the pressure history against gridded atmospheric models used by meteorological forecasting agencies. For example, the pressure grid provided by the Rapid Update Cycle Surface Assimilation System ("RSAS") maintained by the National Oceanic and Atmospheric Administration ("NOAA") may be used as a reference, which provides a grid covering the continental United States, Canada and Alaska and provides atmospheric parameters (including sea-level and surface pressure) on an hourly basis with a grid resolution of 15 km. FIG. 6 illustrates an example of a gridded pressure map that may be obtained from the RSAS.

In one embodiment, correlating the measurement data with one or more atmospheric pressure distribution maps (Step S102) is accomplished using a minimization of variance technique. For each possible location on the pressure distribution map, the time series of pressure is compared against the collected pressure traces stored in the Data Storage and Controller 104 of the Geo-Locator 100. The comparison may be the standard deviation or variance of the differences in pressure. The location is then determined by selecting the point of minimum variance. In one embodiment, sub-grid resolution may be achieved by interpolation in either the variance or the pressure domains.

Naturally occurring pressure variations associated with weather contain sufficient variability that unique and highly accurate position estimates may be obtained after a short period of data collection (e.g., a few days). This approach is aided by the availability of high-quality world-wide pressure data from the weather forecasting community. Datasets such as RSAS from NOAA and Modern Era Retrospective—Analysis for Research and Applications (MERRA) from NASA provide ground truth for barometric pressure over the U.S. and the globe respectively.

An exemplary operation of the System 1 will now be described with reference to FIGS. 1-3 and 5-7. In this particular example, based on actual trials, a commercial-off-the-shelf ("COTS") MEMS pressure logger, the MSR160 (available from MSR Electronics™ and shown in FIG. 5), was used as the Geo-locator 100. In Step S101 the MSR160 was positioned in a desk drawer inside the Charles Stark Draper Laboratory, in Cambridge, Mass., and collected pressure measurement data for 3.8 days. In Step S102, the pressure measurement data was then correlated against the atmospheric pressure distribution maps available in the RSAS database for North America and the surrounding ocean. In Step S103, the Location Processor 200 determined a location within 3 km of the actual location of the Geo-locator 100. A half week of logged data was more than sufficient to ensure zero false detections (although 9 hours of data is typically sufficient for a unique location solution over the entire RSAS dataset with no prior position estimate). Table 1 illustrates the typical accuracy of a determined location using the RSAS dataset with varying time periods for gathering pressure measurements:

TABLE 1

| Time Period (days) | Accuracy of Determined Location |
|---|---|
| 3.8 | 3 km |
| 7 | 1.8 km |
| 9 | ~0 km |

The overall accuracy of the determined location depends on the grid spacing (i.e., resolution) of the dataset used to determine the location of the Geo-locator 100. For example, the RSAS dataset typically has a grid spacing of 13 km. Thus, additional uncertainty may be introduced by the dataset, separate from the uncertainty introduced by the length of time (or lack thereof) over which air pressure measurements are gathered.

Figure 7:
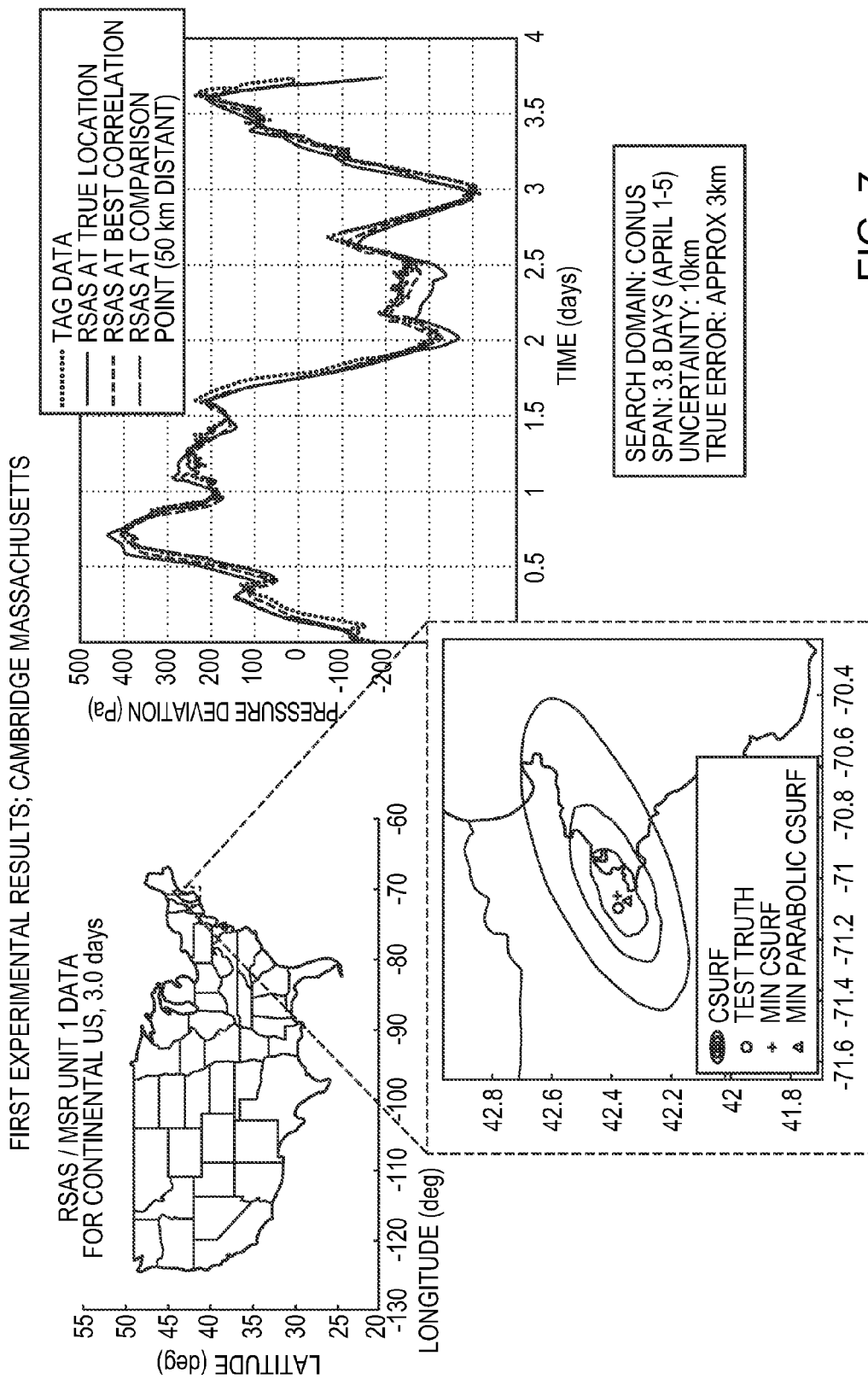
FIG. 7 is an illustration of an exemplary application of the geo-location method illustrated in the flow-chart depicted in FIG. 4.

In one exemplary embodiment, the Location Processor 200 determines the location of the Geo-locator 100 with degrees of confidence. FIG. 7 illustrates exemplary error ellipses that represent the certainty of the determination for various degrees of confidence.

In situations where the tag moves, pressure variations may be recorded at a higher rate (e.g., 1 Hz) and correlated against a topographical database. In one embodiment, the topographical database information may be combined with maps of roads in the approximate area to narrow the required search space.

Figure 8:
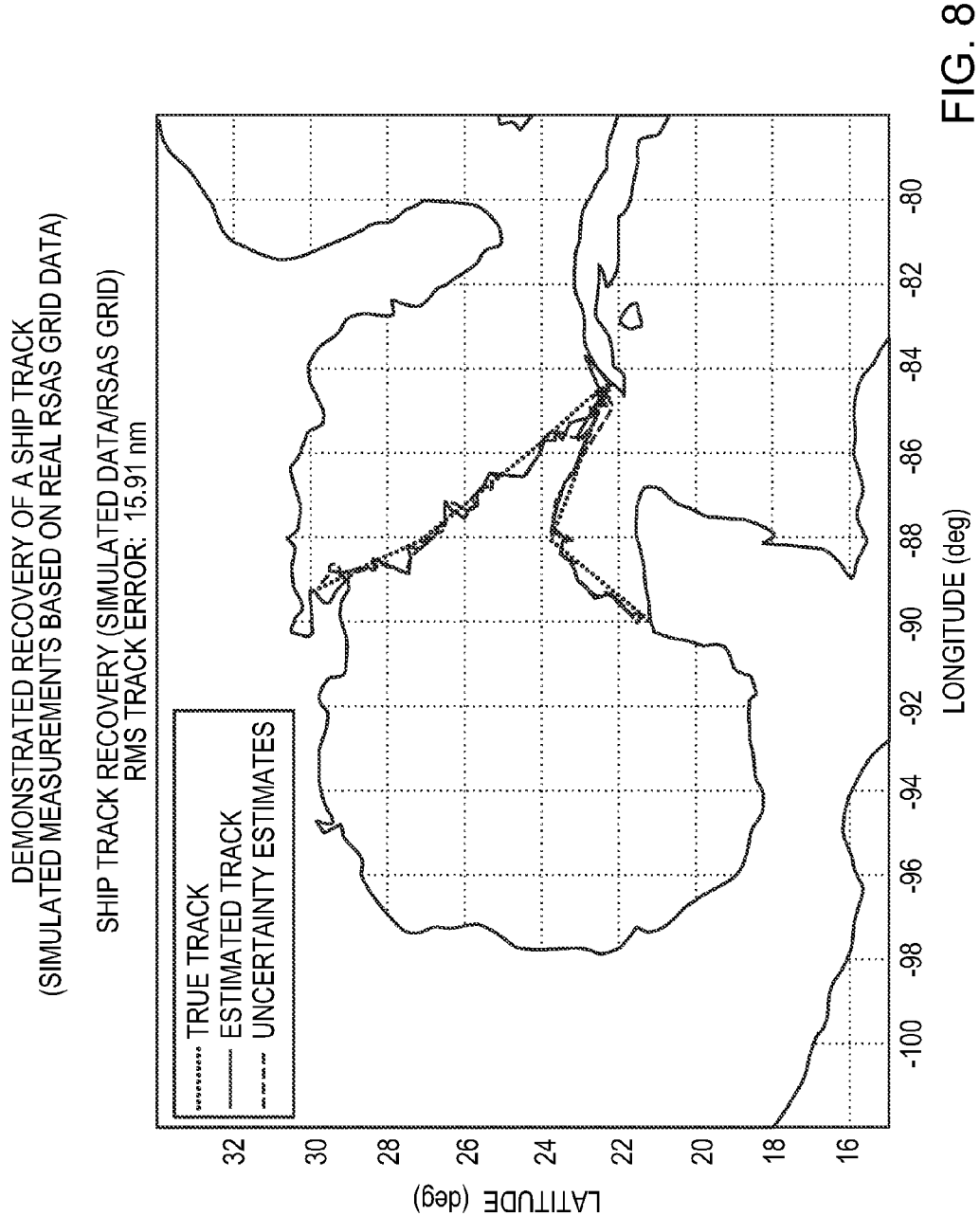
FIG. 8 is an illustration of a map having geo-location information provided thereon for a Geo-locator device of FIG. 2 that is moving.

Barometric pressure logging can also be used to track a moving object (e.g., on a ship, automobile, train, etc.). In one exemplary embodiment, the Location Processor 200 receives the initial (or final) location of the moving object and performance characteristics of the moving object (e.g., maximum speed). FIG. 8 illustrates an example of a directed map created using the location results determined by the Location Processor 200.

According to one embodiment, an iterative Bayesian approach is utilized to determine the location of a moving Geo-locator 100. According to this embodiment, two additional resources are used to determine the location of the moving Geo-locator 100: a Probability Map and a Propagator Function. A Probability Map is a grid of positions (latitude/longitude), with each position having an associated probability. The probability represents the likelihood that the Geo-locator 100 was at a location associated with that position on the probability map. A Propagator Function is a probability distribution function that indicates the likelihood that the tag can be found at location Y, given a starting location X, and a propagation time T. For instance, assume that a ship averages travel at 10 knots, and has a maximum speed of 25 knots. After one hour the propagator function would be a radially symmetric function resembling a "top hat" with a mean radius of 10 nautical miles, and a value of zero beyond a 25 nautical mile radius. The propagator function is normalized to have a value of unity.

Figure 4:
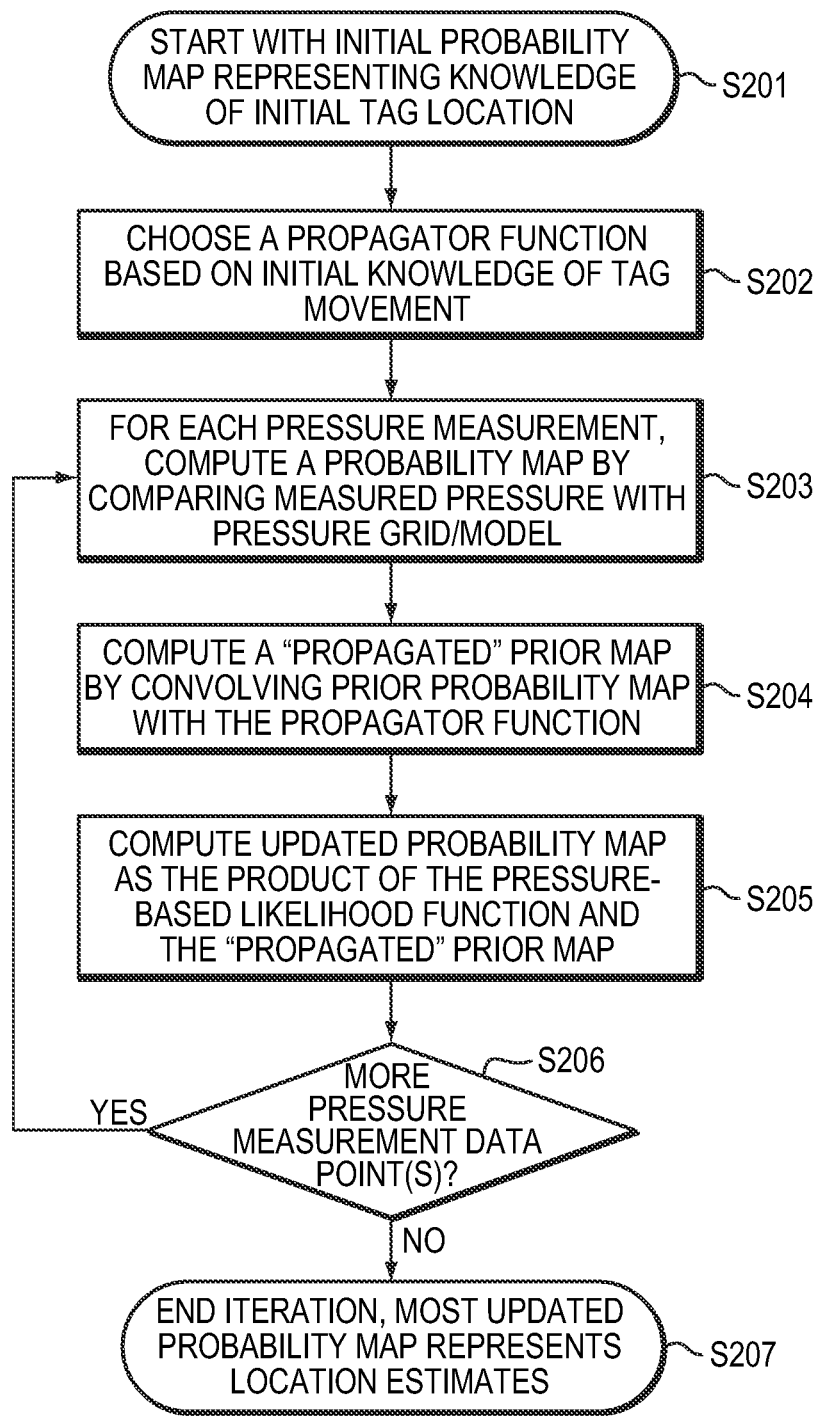
FIG. 4 is a flow-chart illustrating a method for determining the geo-location of a device that incorporates an iterative Bayesian approach according to an exemplary embodiment of the invention.
Figure 5:
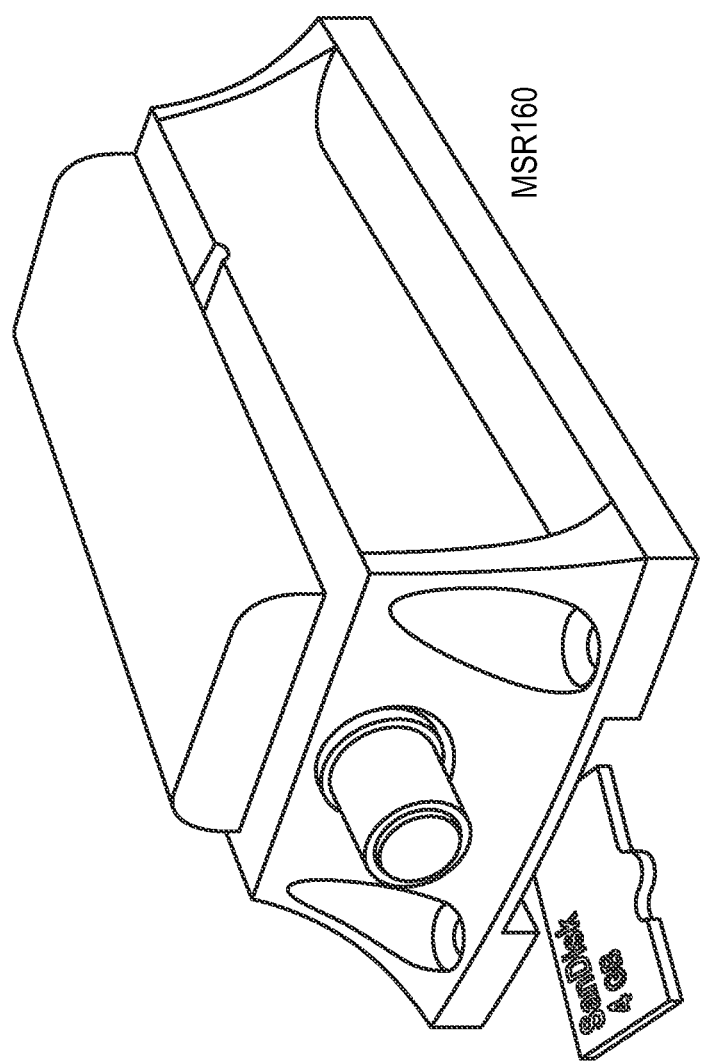
FIG. 5 is an illustration of a tag according to an exemplary embodiment of the invention.

The iterative Bayesian approach will now be described with reference to FIGS. 1, 2 and 4. The process starts with an initial probability map and the initial position of the Geo-locator 100 (Step S201). This may be a delta function for a known starting location, or it may be a uniform prior probability distribution for a completely unknown initial position. Next, a Propagator Function is chosen based on initial knowledge—e.g. that a tag is on a cargo ship capable of no more than 30 knots (Step S202). Next, for each time at which a pressure measurement is available, compute a Probability Map based on comparing the measured pressure with the available pressure grid (Step S203). The likelihood function (L) that the Geo-Locator 100 was at a particular position on the pressure grid is calculated as follows:

$$L \propto \exp\left(-\left(\frac{P_{meas} - P_{grid}}{\sigma}\right)^2\right) \quad \text{(Equation 1)}$$

where $P_{meas}$ is the measured pressure; $P_{grid}$ is the grid pressure at that point, and $\sigma$ is the estimated measurement uncertainty.

Next, given the prior probability map, a "propagated" prior map is computed by convolving the map with the propagator function utilizing the standard mathematical convolution operator (Step S204). Next, an a-posteriori probability map is computed as the product of the pressure-based likelihood function and the propagated prior map (Step S205). This new probability map is the new estimated position.

The process is iterated when a new measurement becomes available (Step S206): the probability map computed in Step S203 becomes the new prior map, and the propagator function is computed given the time elapsed since the last measurement. In one embodiment, the algorithm described above may be executed backwards in time (i.e., propagating the map using the measurements in reverse time order), using a known ending location to determine the Geo-locator's 100 original location.

In another embodiment, the Location Processor 200 determines the location of the moving object without precise knowledge of the initial or final location of the moving object. Instead the Location Processor 200 begins with the earliest known data point and runs the iterative Bayesian algorithm (described above) executing forward in time to generate a first set of probability maps. Next, the Location Processor 200 runs the iterative Bayesian algorithm backwards in time starting with the latest known data point to generate a second set of probability maps. The Location Processor 200 then determines a final "best estimate" for the geo-location at each time step by multiplying the two sets of generated maps.

There are a wide variety of applications for the invention described herein. The tags implementing the invention may be attached to packaging and shipping containers and may be used to monitor their movement paths, and detect unauthorized diversion, substitution, or other illicit activity. Other potential users include both national organizations (homeland security, customs agencies) and corporate users interested in monitoring the integrity of their supply chains.

Another area of use is in law enforcement, tags consistent with the exemplary embodiments of the invention may be used to monitor people and paraphernalia (e.g., to determine smuggling routes or similar illegal activities).

A potential combined application is to add a pressure-sensing capability to a common GPS-based location tag (such as is used in fleet tracking applications for large commercial shipping companies); the pressure sensor fills in location information between GPS updates. This allows for less frequent GPS fixes, with the associated reduction in power consumption.

The terms and expressions employed herein are used as terms of description and not of limitation and there is no intention, in the use of such terms and expressions, of excluding any equivalents of the features shown and described or portions thereof, but it is recognized that various modifications are possible within the scope of the invention claimed. For example, although some of the examples presented refer to tags and devices, one of ordinary skill in the art will recognize that embodiments of the present invention also encompass other geo-positioning devices.

Therefore, it must be expressly understood that the illustrated embodiments have been shown only for the purposes of example and should not be taken as limiting the invention, which is defined by the following claims. The following claims are thus to be read as not only literally including what is set forth by the claims but also to include all equivalents that are insubstantially different, even though not identical in other respects to what is shown and described in the above illustrations. In particular, it should be understood that the order of steps or order for performing certain actions is immaterial so long as the invention remains operable. Moreover, two or more steps or actions may be conducted simultaneously.

APPENDIX A

Derivation

In the following, the device to be tracked will be denoted a "data logger." The data logger may include a barometer, clock, memory, and power supply. Additional sensors may be employed in an effort to increase tracking accuracy. For example, a three-axis MEMS accelerometer and/or a three-axis magnetometer may be employed. It will be assumed in the following that the only available sensor is a barometer.

It is assumed that the data logger is retrieved after its journey for post-processing. As a result, a solution may rely on statistical smoothing techniques. For example, a common approach is to employ a forward filter and a backward filter, with the solution found by combining the results of the two filters.

A.1 Problem Definition
Data Logger Measurements
The scalar pressure measurement at time t is modeled as $$y_t = P_t(r_t) + z_t + n_t, \quad (3.1.1)$$

where $P_t(r_t)$ is the true pressure at data logger position $r_t$, $n_t$ is zero-mean white noise, independent of $r_t$, and $z_t$ is zero-mean colored noise, independent of $r_t$. The parameter $z_t$ can be modeled as a constant bias or a time-varying measurement error.

The entire set of data logger pressure measurements is denoted by $$Y = \{y_1, y_2, \ldots, y_n\}, \quad (3.1.2)$$

where $y_i$ is the pressure measurement at time $t_i$, and the set of measurements up to and including $y_i$ is $$Y_i = \{y_1, y_2, \ldots, y_i\}, \quad (3.1.3)$$

State Vector
The data logger state vector used here is $$x_t = \begin{bmatrix} r_t \\ v_t \\ z_t \end{bmatrix}, \quad (3.1.4)$$

where $v_t$ is data logger velocity.
The entire data logger state vector path is denoted by $$X = \{x_t; t \in T\}, \quad (3.1.5)$$

State Vector Dynamics
We assume that $z_t$ is a first-order Markov process so that, in Ito form, $$dz_t = -\frac{1}{\tau_z(t)} z_t dt + d\beta_{z,t}. \quad (3.1.6)$$

where $\{\beta_{z,t}; t \in T\}$ is a scalar Brownian motion process with $E\{d\beta_{z,t}^2\} = q_z(t)dt$. The estimated parameters $\tau_z(t)$ and $q_z(t)$ and can be varied over time as part of the design process. It is expected that a substantial bias may be present in the data logger measurements. For time intervals for which altitude is constant, it is expected that the bias will be the major contributor to $z_t$. However, if the data logger altitude suddenly changes, $z_t$ may change accordingly, since the historical database may not include different altitudes. In practice, measurement residuals could be monitored in an attempt to detect such changes. Compensation could then be applied by re-initialization or changing the parameter values (e.g., lowering $\tau_z(t)$ and/or increasing $q_z(t)$).

The state vector dynamics are modeled by $$dx_t = F(t)x_t dt + Gd\beta_t, \text{ where} \quad (3.1.7),$$

$$F(t) = \begin{bmatrix} 0 & I & 0 \\ 0 & 0 & 0 \\ 0 & 0 & -1/\tau_z(t) \end{bmatrix}, \quad (3.1.8)$$

$$G = \begin{bmatrix} 0 & 0 \\ I & 0 \\ 0 & 1 \end{bmatrix},$$

$$d\beta_t = \begin{bmatrix} d\beta_{v,t} \\ d\beta_{z,t} \end{bmatrix},$$

and $\{\beta_{v,t}; t \in T\}$ is a vector Brownian motion process with $E\{d\beta_{v,t}^2\} = Q_v(t)dt$. The matrix $(Q_v(t))$, which is an estimate of the velocity driving noise strength, can be varied over time as part of the design process.

Objective

The primary objective is the calculation of the conditional probability density p(X|Y). In the following, we take the approach of combining forward and backward filtering solutions to obtain the final track estimate. We consider the design of the forward filter first. The design of the backward filter is straightforward once the design of the forward filter is completed.

The forward filter calculates the conditional probability densities $\{p(x_t|Y_i); t \leq t_i, i=1, 2, \ldots, n\}$ recursively. Forward filter implementation is carried out in two steps: (1) propagation between measurements, and (2) measurement updating.

A.2 Forward Propagation: Continuous-Time

Data logger motion in continuous time can be accounted for by using Kolmogorov's forward equation. Assume that the dynamics satisfy the vector Ito stochastic differential equation $$dx_t = f(x_t,t)dt + G(x_t,t)d\beta_t, \quad (3.2.1)$$

where $\{\beta_t; t \in T\}$ is a vector Brownian motion process with $E\{d\beta_t d\beta_t^T\} = Q(t)dt$. Equation (3.2.1) is a vector Markov process.

The probability density function evolves according to the forward Kolmogorov equation:

$$\frac{\partial p}{\partial t} = -\sum_{i=1}^{n} \frac{\partial [pf_i]}{\partial x_i} + \frac{1}{2} \sum_{i,j=1}^{n} \frac{\partial^2 [p(GQG^T)_{ij}]}{\partial x_i \partial x_j}. \quad (3.2.2)$$

If $GQG^T$ is independent of x, this becomes $$\frac{\partial p}{\partial t} = -\sum_{i=1}^{n} \frac{\partial [pf_i]}{\partial x_i} + \frac{1}{2} \sum_{i,j=1}^{n} (GQG^T)_{ij} \frac{\partial^2 p}{\partial x_i \partial x_j} \quad (3.2.3)$$

$$= -\sum_{i=1}^{n} \frac{\partial [pf_i]}{\partial x_i} + \frac{1}{2} tr[(GQG^T)p_{xx}],$$

where $$(p_{xx})_{ij} = \frac{\partial^2 p}{\partial x_i \partial x_j}.$$

Linear System

For a linear system, the dynamics are $$dx_t = F(t)x_t dt + G(t)d\beta_t, \quad (3.2.4)$$

where $G(t)$ is independent of $x_t$. Then the forward Kolmogorov equation is $$\frac{\partial p}{\partial t} = -p\,trF - p_x^T Fx + \frac{1}{2} tr[(GQG^T)p_{xx}], \quad (3.2.5)$$

where $$(p_x)_i = \frac{\partial p}{\partial x_i}.$$

Using the model of (3.1.6) and (3.1.7) gives $$\frac{\partial p}{\partial t} = \frac{1}{\tau_z(t)} p - \frac{\partial p}{\partial r} v + \frac{1}{2} tr\left[Q_v \frac{\partial^2 p}{\partial v^2}\right] + q_z \frac{\partial^2 p}{\partial z^2}. \quad (3.2.6)$$

A.3 Measurement Updating

Consider the process of updating the conditional probability density at measurement time $t=t_i$ by incorporating the measurement $y_i$. The a priori density is $p(x_i|Y_{i-1})$ and the posterior density is $p(x_i|Y_i)$. The measurement update at time is implemented using Bayes' rule:

$$p(x_i|Y_i) = \frac{1}{a_i} p(y_i|x_i) p(x_i|Y_{i-1}); \; x_i \in R_{xi}, \quad (3.3.1)$$

where $$a_i = \int_{x_i \in R_{xi}} dx_i p(y_i|x_i) p'(x_i), \quad (3.3.2)$$

and $R_{xi}$ is the range space of $x_i$.

Using the measurement model in (3.1.1), the a priori measurement estimate conditioned on the hypothesis $x_i = x$ is $$y_i'(x) = P_i'(r) + z, \quad (3.3.3)$$

where $P_i'(r)$ is the estimated pressure at time $t_i$, conditioned on the hypotheses $r_i = r$.

The measurement residual is $$v_i(x) = y_i - y_i'(x) \quad (3.3.4)$$

$$= P_i(r_i) - P_i'(r) + z_i - z + n_i.$$

Since the available pressure measurements from the historical database are quantized in both space and time, the estimate $P_i'(r)$ must be obtained using interpolation in both space and time.

Denote the historical database pressure measurements by $$\tilde{P}^G = \{\tilde{P}(t_i^G, r_j^G; i=1,2,\ldots,n_t^G, j=1,2,\ldots,n_r^G\}. \quad (3.3.5)$$

The measurements are related to the true values by $$\tilde{P}^G = P^G + E_P^G, \quad (3.3.6)$$

where $E_P^G$ represents the errors associated with historical database.

Now, denote the estimate $P_i'(r)$ by $$P_i'(r) = \text{interp}\{r, t_i | \tilde{P}^G\} = \text{interp}\{r, t_i | P^G + E_P^G\}. \quad (3.3.7)$$

We can then express $P_i'(r)$ as $$P_i'(r) = P_i(r) + e_{r,t_i}^{interp} + e_{r,t_i}^{G}, \quad (3.3.8)$$

where $e_{r,t_i}^{interp}$ is the interpolation error, and $e_{r,t_i}^{G}$ is the interpolated historical database error.

Putting (3.3.8) into (3.3.4) gives $$v_i(x) = z_i - z - e_{r,t_i}^{interp} - e_{r,t_i}^{G} + n_i. \quad (3.3.9)$$

Since $e_{r,t_i}^{interp}$ and $e_{r,t_i}^{G}$ are random variables, we require statistical models of them in order to proceed. In practice these errors may be correlated over time. While this can be handled in the filtering theory, it introduces unnecessary complexity. Correlated components of $e_{r,t_i}^{interp}$ and $e_{r,t_i}^{G}$ are best handled by adding them to the state vector. At the moment, the correlation structure of these errors is unknown. Thus, we will assume in the following that $e_{r,t_i}^{interp}$ and $e_{r,t_i}^{G}$ are mutually independent zero-mean white noise processes and lump them with $n_i$, which is also a zero-mean white noise process. Thus, (3.3.9) becomes $$\upsilon_i(x)z_i - z + w_i, \tag{3.3.10}$$

where $w_i = n_i - e_{r,t_i}^{interp} - e_{r,t_i}^{G}$ is assumed to be a zero-mean white noise process with rms value $\sigma_{w,i}$.

Let $e_{z,i}(x) = z_i - z$. Then $$\upsilon_i(x) = e_{z,i}(x) + w_i. \tag{3.3.11}$$

where $e_{z,i}(x)$ is a random variable since $z_i$ is unknown. We will assume that $e_{z,i}(x)$ has zero mean and rms value $\sigma_{z,i}$, and is independent of $w_i$. With these assumptions $\upsilon_i(x) = e_{z,i}(x) + w_i$ is a zero-mean random variable with variance $\sigma_{\upsilon,i}^2 = \sigma_{w,i}^2 + \sigma_{z,i}^2$, and $$p(y_i|x_i) = p_{\upsilon,i}(y_i - y_i'(x_i)). \tag{3.3.12}$$

Then the Bayes' update equation becomes $$p(x_i | Y_i) = \frac{1}{a_i} p_{\upsilon,i}(y_i - y_i'(x_i))p(x_i | Y_{i-1}); \tag{3.3.13}$$

$$x_i \in R_{xi},$$

where $p_{\upsilon,i}(\bullet)$ is the probability density of $\upsilon_i$.

Note that the state vector range space $R_{xi}$ has been indexed by time. This is the result of the assumption that the individual subspaces for r, v and z may be pruned as time progresses due to peaking of the individual probability densities. This would allow elimination of regions for which probabilities are small and very unlikely to increase in the future.

A.4 Track Estimation

Data logger state vector estimates at any time can be accomplished using several criteria. The most obvious ones are maximum likelihood and conditional mean.

The maximum likelihood estimate at time $t_i$ is $$\hat{x}_{ML} = \underset{x}{\operatorname{argmax}}\{p_i(x)\}, \tag{3.4.1}$$

and the conditional mean estimate is $$\hat{x}_{CM} = \int_{x \in R_{xi}} dx\, x p_i(x). \tag{3.4.2}$$

The conditional mean estimate requires much more computation than the maximum likelihood estimate, but conceptually is more accurate, in the sense that it minimizes the variance of the estimation errors. However, these statements rely on the fidelity of the models used, i.e., how well they model the actual world. It is not clear at this point which of these is preferred, or if there is another, more preferable approach. For example, the k most likely solutions could be statistically combined in some manner.

With either estimate, the state vector covariance matrix can then be calculated as $$P_x = \int_{x \in R_{xi}} dx (x - \hat{x})(x - \hat{x})^T p_i(x), \tag{3.4.3}$$

and used to estimate the error performance.

A.5 Forward Propagation: Discrete-Time

Probability density propagation is necessarily performed in discrete time. While it is possible to discretize the continuous-time equations given in Section A.2, it may be preferable in practice to utilize the discrete-time equations directly.

Data logger motion in discrete time may be accounted for by using the Chapman-Kolmogorov equation, $$p(x_{i+1}|Y_i) = \int dx_i\, p(x_{i+1}|x_i, Y_i) p(x_i|Y_i). \tag{3.5.1}$$

The data logger state vector is $$x_t = \begin{bmatrix} r_t \\ v_t \\ z_t \end{bmatrix}, \tag{3.5.2}$$

Position and velocity will be modeled by the first-order dynamical models $$r_{i+1} = r_i + v_i \Delta t_i, v_{i+1} = v_i + \Delta v_i. \tag{3.5.3}$$

The colored measurement noise $z_i$ will be modeled as a discrete first-order Markov process:

$$z_{i+1} = \phi_i z_i + q_{z,i}, \tag{3.5.4}$$

where $|\phi_i| < 1$, and $q_{z,i}$ is zero-mean discrete white noise with rms value $\sigma_{qz,i}$. In view of (3.5.3) and (3.5.4), (3.5.1) becomes $$p(x_{i+1}|Y_i) = \int dx_i\, p(x_{i+1}|x_i) p(x_i|Y_i). \tag{3.5.5}$$

Now consider a quantized state space in which $r_i = \{r_{i,1}, r_{i,2}, \ldots, r_{nr_i}\}$, $v_i = \{v_{i,1}, v_{i,2}, \ldots, v_{nv_i}\}$, $z_i = \{z_{i,1}, z_{i,2}, \ldots, z_{nz_i}\}$. Then, $$p(r_{i+1,j}, v_{i+1,k}, z_{i+1,m} | Y_i) = \tag{3.5.6}$$

$$\sum_{a,b,c} p(r_{i+1,j}, v_{i+1,k}, z_{i+1,m} | r_{i,a}, v_{i,b}, z_{i,c}) \times p(r_{i,a}, v_{i,b}, b_{i,c} | Y_i) =$$

$$\sum_{a,b,c} p(r_{i+1,j} | v_{i+1,k}, z_{i+1,m}, r_{i,a}, v_{i,b}, z_{i,c})$$

$$p(v_{i+1,k}, z_{i+1,m} | r_{i,a}, v_{i,b}, z_{i,c}) \times p(r_{i,a}, v_{i,b}, z_{i,c} | Y_i);$$

$$j \in J_i, k \in K_i, m \in M_i,$$

where $J_i, K_i, M_i$ are, respectively, the index sets for $r_i, v_i, z_i$. The summations are over $a \in J_i$, $b \in K_i$, $c \in M_i$.

Using the dynamical constraint $r_{i+1} = r_i + v_i \Delta t_i$ gives $$p(r_{i+1,j}, v_{i+1,k}, z_{i+1,m} | Y_i) = \tag{3.5.7}$$

$$\sum_{a,b,c} p(r_{i+1,j} | r_{i,a}, v_{i,b}) p(v_{i+1,k}, b_{i+1,m} | r_{i,a}, v_{i,b}, z_{i,c}) \times$$

$$p(r_{i,a}, v_{i,b}, z_{i,c} | Y_i) =$$

$$\sum_{a,b,c} p(r_{i+1,j} | r_{i,a}, v_{i,b}) p(v_{i+1,k} | z_{i+1,m}, r_{i,a}, v_{i,b}, z_{i,c})$$

-continued
$$p(z_{i+1,m} | r_{i,a}, v_{i,b}, z_{i,c}) \times p(r_{i,a}, v_{i,b}, z_{i,c} | Y_i).$$

Using the dynamical constraint $v_{i+1}=v_i+\Delta v_i$ gives $$p(r_{i+1,j}, v_{i+1,k}, z_{i+1,m} | Y_i) = \sum_{a,b,c} p(r_{i+1,j} | r_{i,a}, v_{i,b}) p_{\Delta v,i}(v_{i+1,k} - v_{i,b}) \quad (3.5.8)$$
$$p(z_{i+1,m} | r_{i,a}, v_{i,b}, z_{i,c}) \times p(r_{i,a}, v_{i,b}, z_{i,c} | Y_i).$$

where $p_{\Delta v,i}(\bullet)$ is the probability density of the velocity change $\Delta v_i$.

Using the dynamical constraint $z_{i+1}=\phi_i z_i+q_{z,i}$ gives $$p(r_{i+1,j}, v_{i+1,k}, z_{i+1,m} | Y_i) = \sum_{a,b,c} p(r_{i+1,j} | r_{i,a}, v_{i,b}) \quad (3.5.9)$$
$$p_{\Delta v,i}(v_{i+1,k} - v_{i,b}) p_{qz,i}(z_{i+1,m} - \phi_i z_{i,c}) \times p(r_{i,a}, v_{i,b}, z_{i,c} | Y_i),$$

where $p_{qz,i}(\bullet)$ is the probability density of $q_{z,i}$.

In view of (3.5.3), we can express the first term inside the summation in (3.5.9) as $$p(r_{i+1,j} | r_{i,a}, v_{i,b}) = \tilde{\delta}(r_{i+1,j} - r_{i,a} - v_{i,b} \Delta t_i) \quad (3.5.10)$$

where $\tilde{\delta}(\bullet)$ is a "soft" delta function:

$$\tilde{\delta}(r_{i+1,j} - r_{i,a} - v_{i,b} \Delta t_i) = \quad (3.5.11)$$
$$\begin{cases} 1; & b = \arg\min_{\beta \in K_i}(\|r_{i+1,j} - r_{i,a} - v_{i,\beta}\Delta t_i\|) \\ 0; & \text{otherwise} \end{cases}.$$

The soft form of the delta function is required to compensate for the quantization of the velocity vector; a hard delta function would yield zero with probability ~1.

Let $\tilde{b}_i$ be the minimizing index found in (3.5.11). Then, (3.5.9) becomes $$p(r_{i+1,j}, v_{i+1,k}, z_{i+1,m} | Y_i) = \sum_{a,c} p_{\Delta v,i}(v_{i+1,k} - v_{i,\tilde{b}_i}) \quad (3.5.12)$$
$$p_{qz,i}(z_{i+1,m} - \phi_i z_{i,c}) p(r_{i+1,j} - r_{i,a}, v_{i,\tilde{b}_i}, z_{i,c} | Y_i).$$

Special Case: Pure Measurement Bias

If the correlated measurement error $z_i$ is a constant bias, then $\phi_i=1$, $p_{qz,i}(\bullet)=\delta(\bullet)$, and $$p(r_{i+1,j}, v_{i+1,k}, z_{i+1,m} | Y_i) = \quad (3.5.13)$$
$$\sum_a p_{\Delta v,i}(v_{i+1,k} - v_{i,\tilde{b}_i}) p(r_{i+1,j} - r_{i,a}, v_{i,\tilde{b}_i}, z_{i,m} | Y_i).$$

A.6 Forward Propagation: Discrete-Time, No Velocity Estimation

Estimation of data logger velocity may be problematic in some scenarios; for example, when there are significant shifts in velocity or measurement errors. In such cases, a reduced state space size may be preferable. Even if velocity is not estimated, it may still be possible to use known velocity constraints to advantage. For example, a ship at sea is subject to known upper limits on speed.

The data logger state vector is $$x_t = \begin{bmatrix} r_t \\ z_t \end{bmatrix}, \quad (3.6.1)$$

and the propagation equation becomes $$p(r_{i+1,j}, z_{i+1,m} | Y_i) = \sum_{a,c} p(r_{i+1,j}, z_{i+1,m} | r_{i,a}, z_{i,c}) p(r_{i,a}, z_{i,c} | Y_i) = \quad (3.6.2)$$
$$\sum_{a,c} p(r_{i+1,j} | z_{i+1,m}, r_{i,a}, z_{i,c}) p(z_{i+1,m} | r_{i,a}, z_{i,c}) p(r_{i,a}, z_{i,c} | Y_i) =$$
$$\sum_{a,c} p(r_{i+1,j} | r_{i,a}) p_{qz,i}(z_{i+1,m} - \phi_i z_{i,c}) p(r_{i,a}, z_{i,c} | Y_i).$$

Now we employ the speed constraint $s_i \|v_i\| \leq s_{max,i}$ to get $$p(r_{i+1,j} | r_{1,a}) = \begin{cases} \gamma_{i,j}; & \|r_{i+1,j} - r_{i,a}\| < s_{max,i}\Delta t_i \\ 0; & \text{otherwise} \end{cases}. \quad (3.6.3)$$

Let $S_{i,j}=\{s; \|r_{i+1,j} - r_{i,s}\| < s_{max,i}\Delta r_i\}$. Then $\gamma_{i,j}=1/\text{card}(S_{i,j})$. Thus, $$p(r_{i+1,j}, z_{i+1,m} | Y_i) = \gamma_{i,j} \sum_{s \in S_{i,j}, c} p_{qz,i}(z_{i+1,m} - \phi_i z_{i,c}) p(r_{i,s}, z_{i,c} | Y_i). \quad (3.6.4)$$

Special Case: Pure Measurement Bias

If the correlated measurement error $z_i$ is an unknown constant, then $$p(r_{i+1,j}, z_{i+1,m} | Y_i) = \gamma_{i,j} \sum_{s \in S_{i,j}} p(r_{i,s}, z_{i,m} | Y_i). \quad (3.6.5)$$

A.7 Measurement Differencing: Continuous-Time

If the measurement error $z_t$ is an unknown constant, then it can be eliminated by measurement differencing. From (3.1.1), the measurements are modeled by $$y_t = P_t(r_t) + z + n_t, \quad (3.7.1)$$

where $z$ is constant and $n_t$ is white noise.

The data logger state vector is $$x_t = \begin{bmatrix} r_t \\ v_t \end{bmatrix}. \quad (3.7.2)$$

Then the measurement is $$\dot{y}_t = \frac{\partial P}{\partial t}(t, r_t) + \frac{\partial P}{\partial r}(t, r_t) v_t + \dot{n}_t. \quad (3.7.3)$$

This equation, sometimes called a Langevin equation, is a formal representation, since the derivative of white noise does not exist. However, this equation indicates that we need to calculate pressure gradients with respect to both time and space in order to process measurement differences.

A.8 Measurement Differencing: Discrete-Time

We again assume that $z_t$ is an unknown constant. The data logger state vector is $$x_t = \begin{bmatrix} r_t \\ v_t \end{bmatrix}. \tag{3.8.1}$$

In discrete time, we have measurements $$y_i = P(t_i, r_i) + z + n_i, \tag{3.8.2}$$

and $$y_{i+1} = P(t_{i+1}, r_{i+1}) + z + n_{i+1}, \tag{3.8.3}$$

where $n_i$ is discrete white noise with zero mean and variance $\sigma_{n,i}^2$.

Differencing gives, to first order, $$\begin{aligned} \delta y_{i+1} &= y_{i+1} - y_i \tag{3.8.4} \\ &= P(t_{i+1}, r_{i+1}) - P(t_i, r_i) + n_{i+1} - n_i \\ &\approx \frac{\partial P}{\partial t}(t_i, r_i)\Delta t_i + \frac{\partial P}{\partial r}(t_i, r_i)v_i\Delta t_i + \delta n_i, \end{aligned}$$

where $\delta t_i = t_{i+1} - t_i$, $v_i$ is velocity, and $\delta n_i = n_{i+1} - n_i$ is discrete white noise with zero mean and variance $\sigma_{n,i+1}^2 + \sigma_{n,i}^2$.

The a priori estimate of $\delta y_{i+1}$ conditioned on $x_i = x$ is $$\delta y'_{i+1} = \frac{\partial P'}{\partial t}(t_i, r)\Delta t_i + \frac{\partial P'}{\partial r}(t_i, r)v\Delta t_i, \tag{3.8.5}$$

where $$\frac{\partial P'}{\partial t}(t_i, r)$$

and $$\frac{\partial P'}{\partial r}(t_i, r)$$

are estimated pressure gradients calculated by interpolating the historical database measurements at times in the neighborhood of $t_i$, and grid locations in the neighborhood of $r$.

The measurement residual is $$\begin{aligned} \upsilon_{i+1}(x) &= \delta y_{i+1} - \delta y'_{i+1}(x) \tag{3.8.6} \\ &\approx \left[\frac{\partial P}{\partial t}(t_i, r_i) - \frac{\partial P'}{\partial t}(t_i, r)\right]\Delta t_i + \\ &\quad \left[\frac{\partial P}{\partial r}(t_i, r_i)v_i - \frac{\partial P'}{\partial r}(t_i, r)v\right]\Delta t_i + \delta n_i \\ &= e_{Pgt}(t_i, r_i, r)\Delta t_i + e_{Pgr}(t_i, r_i, r, v)\Delta t_i + \delta n_i. \end{aligned}$$

The temporal pressure gradient error $e_{Pgt}(t_i, r_i, r)$ includes the effects of uncertainties in the historical database and interpolation errors, and depends on the hypothesized data logger position. The spatial pressure gradient error $e_{Pgr}(t_i, r_i, r, v)$ includes the effects of uncertainties in the historical database and interpolation errors, and depends on both the hypothesized data logger position and velocity.

Since $e_{Pgt}(t_i, r_i, r)$ and $e_{Pgr}(t_i, r_i, r, v)$ are random variables, we require statistical models of them in order to proceed. We assume that these errors are mutually independent zero-mean white noise processes with respective rms values $\sigma_{Pgt,i}$ and $\sigma_{Pgr,i}$. We can lump these errors with $\delta n_i$, which is also a zero-mean white noise process. With these assumptions, $\upsilon_{i+1}(x)$ becomes a zero-mean discrete white noise process with variance $\sigma_{\upsilon,i+1}^2 = \sigma_{Pgt,i}^2 + \sigma_{n,i+1}^2 + \sigma_{n,i}^2$.

Then the Bayes' update equation becomes $$p(x_i \mid \Delta Y_{i+1}) = \frac{1}{a_i} p_{\upsilon,i+1}(\delta y_{i+1} - \delta y'_{i+1}(x_i))p(x_i \mid \Delta Y_i); \tag{3.8.7}$$

$$x_i \in R_{xi},$$

where $p_{\upsilon,i}(\bullet)$ is the probability density of $\upsilon_i$, and $\Delta Y_i = \{\delta y_2, \delta y_3, \ldots, \delta y_i\}$. Note that the measurement $\delta y_{i+1}$ at time $t_{i+1}$ is used to update the state at time $t_i$.

A.9 Measurement Differencing: Discrete-Time, No Velocity Estimation

Now consider the case where velocity is not estimated but, as in Section 3.6, we can employ a speed constraint. The data logger state vector is $x_t = r_t$. Under the hypothesis $r_i = r$, the measurement update equation has the form $$p(r \mid \Delta Y_{i+1}) = \frac{1}{a_i} p(\delta y_{i+1} \mid r)p(r \mid \Delta Y_{i-1}); \tag{3.9.1}$$

$$r \in R_{ri},$$

where $R_{ri}$ is the range space of $r$ at time $t_i$.

Now, $$\begin{aligned} p(\delta y_{i+1} \mid r) &= \int_{v \in R_{vi}} dv \, p(\delta y_{i+1}, v \mid r) \tag{3.9.2} \\ &= \int_{v \in R_{vi}} dv \, p(\delta y_{i+1} \mid v, r)p(v \mid r), \end{aligned}$$

where $R_{vi}$ is the range space of the velocity $v$ at time $t_i$ and, from Section 3.8, $$p(\delta y_{i+1} \mid v, r) = p_{\upsilon,i+1}(\delta y_{i+1} - \delta y'_{i+1}(v, r)). \tag{3.9.3}$$

Thus, $$\begin{aligned} p(\delta y_{i+1} \mid r) &= \int_{v \in R_{vi}} dv \, p_{\upsilon,i+1}\{\delta y_{i+1} - \delta y'_{i+1}(v, r)\}p(v \mid r) \tag{3.9.4} \\ &= \int_{v \in R_{vi}} dv \, p_{\upsilon,i+1}\left\{\delta y_{i+1} - \begin{bmatrix} \frac{\partial P'}{\partial t}(t_i, r) + \\ \frac{\partial P'}{\partial r}(t_i, r)v \end{bmatrix}\Delta t_i\right\}p(v \mid r). \end{aligned}$$

Since the velocity $v$ appears explicitly within the assumed residual probability density function, it cannot simply be integrated out of the measurement update equation. The velocity range space is $R_{vi} = \{v: \|v\| \leq s_{max,i}\}$, and is not naturally limited in size. In practice, a suitably small number of hypothesized velocities should be chosen to cover $R_{vi}$ particularly at the boundaries.

As another comment, the probability, $p(v \mid r)$ may not be independent of $r$. For example, the speed limit may depend on whether the data logger is at sea or on land.

APPENDIX B

Computer Implementation Definition

As used herein, references to "a device," a "unit," "a machine" and/or "machines" may include, without limitation, a general purpose computer that includes a processing unit, a system memory, and a system bus that couples various system components including the system memory and the processing unit. The general purpose computer may employ the processing unit to execute computer-executable program modules stored on one or more computer readable media forming the system memory. The program modules may include routines, programs, algorithms, modules, objects, components, data structures, etc., that perform particular tasks or implement particular abstract data types. The invention described herein may be implemented in various computer system configurations, including hand-held wireless devices, such as mobile phones or PDAs, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote computer storage media including memory storage devices.

As used herein, references to "a module," "modules", "function", and/or "algorithm" generally mean, but are not limited to, a software or hardware component that performs certain tasks or steps. A module may advantageously be configured to reside on an addressable storage medium and be configured to execute on one or more processors. A module may be fully or partially implemented with a general purpose integrated circuit (IC), co-processor, field-programmable gale array (FPGA), or application-specific integrated circuit (ASIC). Thus, a module may include, by way of example, components, such as software components, object-oriented software components, class libraries, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules. Additionally, the components and modules may advantageously be implemented on many different platforms, including computers, computer servers, data communications infrastructure equipment such as application-enabled switches or routers, or telecommunications infrastructure equipment, such as public or private telephone switches or private branch exchanges (PBX). In any of these cases, implementation may be achieved either by writing applications that are native to the chosen platform, or by interlacing the platform to one or more external application engines.

Any suitable programming language may be used in accordance with the various embodiments of the invention. Illustratively, the programming language used may include assembly language, Ada, APL, Basic, C, C++, COBOL, dBase, Forth, FORTRAN, Java, Modula-2, Pascal, Prolog, REXX, and/or JavaScript for example. Further, it is not necessary that a single type of instruction or programming language be utilized in conjunction with the operation of the system and method of the invention. Rather, any number of different programming languages may be utilized as is necessary or desirable.

Also, the instructions and/or data used in the practice of the invention may utilize any compression or encryption technique or algorithm, as may be desired. An encryption module might be used to encrypt data. Further, files or other data may be decrypted using a suitable decryption module. Compression algorithms may be a series of instructions in software executed by general-purpose processor, or may be executed in hardware, for example, in a compression specific co-processor. Compression algorithms are well known in the art, but include lossless and lossy compression. Lossless compression algorithms may include Lempel-Ziv Welch (LZW), Lempel-Ziv 1 through 7, arithmetic encoding. Huffman encoding, combinations thereof (e.g., Deflate) or any other lossless encoding algorithm. Lossy compression algorithms may include. MPEG1 through 4, MP3, MP4, Off-the-shelf compression software may be utilized including Gzip™, WinZip™, FZip, DivX, FACC, or any other off-the-shelf compression software.

The computing environment may also include other removable/nonremovable, volatile/nonvolatile computer storage media. For example, a hard disk drive may read or write to nonremovable, nonvolatile magnetic media. A magnetic disk drive may read from or write to a removable, nonvolatile magnetic disk, and an optical disk drive may read from or write to a removable, nonvolatile optical disk such as a CD ROM or other optical media. Other removable/nonremovable, volatile/nonvolatile computer storage media that can be used in the exemplary operating environment include, but are not limited to, magnetic tape cassettes, Hash memory cards, digital versatile disks, digital video tape, solid state RAM, solid state ROM, and the like. The storage media are typically connected to the system bus through a removable or non-removable memory interlace.

The processing unit that executes commands and instructions may be a general purpose computer, but may utilize any of a wide variety of other technologies including a special purpose computer, a microcomputer, mini-computer, mainframe computer, programmed micro-processor, micro-controller, peripheral integrated circuit element, a CSIC (Customer Specific Integrated Circuit), ASIC (Application Specific Integrated Circuit), a logic circuit, a digital signal processor, a programmable logic device such as an FPGA (Held Programmable Gate Array), PLD (Programmable Logic Device), PLA (Programmable Logic Array), RFID integrated circuits, smart chip, or any other device or arrangement of devices that is capable of implementing the steps of the processes of the invention.

It should be appreciated that the processors and/or memories of the computer system need not be physically in the same location. Each of the processors and each of the memories used by the computer system may be in geographically distinct locations and be connected so as to communicate with each other in any suitable manner. Additionally, it is appreciated that each of the processor and/or memory may be composed of different physical pieces of equipment.

A user may enter commands and information into the computer through a user interface that includes input devices such as a keyboard and pointing device, commonly referred to as a mouse, trackball or touch pad. Other input devices may include a microphone, joystick, game pad, satellite dish, scanner, voice recognition device, keyboard, touch screen, toggle switch, pushbutton, or the like. These and other input devices are often connected to the processing unit through a user input interface that is coupled to the system bus, but may be connected by other interface and bus structures, such as a parallel port, game port or a universal serial bus (USB).

Furthermore, the memories of may be arranged inside and outside the computer. For example, in a network, the system memory may include (or be part of) a distributed storage system that provides both storage and file-system, such as network-attached-storage (NAS), or a distributed storage system that provides only storage, such as a storage-area-network (SAN). In the ease of NAS, it may include software capable of file management services, including, without limitation, FreeNAS™, NASLite™, and NexentaStor™. The NAS may contain one or more hard disks, arranged into logical, redundant storage containers or RAID arrays. The NAS may utilize one or more file-based protocols including, without limitation, Network Hie System (NFS), Windows NT™ File System (NTFS), File Allocation Table (FAT), Server Message Block/Common Internet File System (SMB/CIFS), or Apple Filling Protocol (AFP).

In the case of SAN, it may use any number of protocols to communicate between server and storage, including, without limitation, the SCSI protocol, HyperSCSCI protocol, iSCSI protocol, ATA over Ethernet, Fibre channel Protocol, and Fibre Channel over Ethernet.

Information stored on the system memories may be stored in a database. The particular architecture of the database may vary according to the specific type of data, mode of access of the data, or intended use of the data stored in the database; including, without limitation, a row-oriented data-store architecture, a column-based database management system, extensible-markup language, a knowledgebase, a frame database, or combinations thereof. A database management system (DBMS) may organize the storage of the data in the database, tailored for the specific requirements of the present system. The DBMS may use any number of query languages to access the database, including, without limitation, structured query language (SQL).

The database may reside within a single storage device within a single computer, multiple storage devices within a single computer, or multiple storage devices across multiple computers.

One or more monitors or display devices may also be connected to the system bus via an interface. In addition to display devices, computers may also include other peripheral output devices, which may be connected through an output peripheral interface. The computers implementing the invention may operate in a networked environment using logical connections to one or more remote computers, the remote computers typically including many or all of the elements described above.

In addition, various networks may be employed in accordance with embodiments of the invention, including a wired or wireless local area network (LAN) or wide area network (WAN), a wireless personal area network (PAN), and other types of networks. When used in a LAN networking environment, computers may be connected to the LAN through a network interface or adapter. When used in a WAN networking environment, computers typically include a modem or other communication mechanism. Modems may be internal or external, and may be connected to the system bus via a user-input interface, or other appropriate mechanism. Computers may be connected over the Internet, an Intranet, an Extranet, an Ethernet, or any other network that facilitates communications. Any number of transport protocols may be utilized, including, without limitation. User Datagram Protocol (UDP), Transmission Control Protocol (TCP), Venturi Transport Protocol (VTP), Datagram Congestion Control Protocol (DCCP), Fiber Channel Protocol (RUDP), Stream Control Transmission Protocol (SCTP), Reliable User Datagram Protocol (RUDP), and Resource ReSerVation Protocol (RSVP). For wireless communications, communications protocols may include Bluetooth, Zigbee, IrDa or other suitable protocol. Furthermore, components of the systems described herein may communicate through a combination of wired or wireless paths.

The invention claimed is:

1. A method for determining a geo-location of an object, the method comprising:
   comparing a plurality of ambient atmospheric pressure measurements obtained for an object against a gridded atmospheric model; and
   based at least in part on the comparison, determining a geo-location of the object.

2. The method of claim 1, wherein the geo-location of the object is determined without using an externally provided navigation signal.

3. The method of claim 2, wherein the geo-location of the object is determined without using a global positioning system signal.

4. The method of claim 1 further comprising using a pressure sensor, associated with the object, to obtain the plurality of ambient atmospheric pressure measurements for the object.

5. The method of claim 4 further comprising storing the plurality of ambient atmospheric pressure measurements in computer memory.

6. The method of claim 5, wherein the ambient atmospheric pressure is measured and stored in the computer memory as a function of time.

7. The method of claim 1 further comprising compensating for environmentally-induced errors in the pressure measurements.

8. The method of claim 7, wherein compensating for the environmentally-induced errors comprises measuring a temperature in a vicinity of the object.

9. The method of claim 7, wherein compensating for the environmentally-induced errors comprises measuring a humidity in a vicinity of the object.

10. The method of claim 7 further comprising storing a parameter measured to compensate for the environmentally-induced errors in computer memory.

11. The method of claim 10, wherein the parameter is measured and stored in the computer memory as a function of time.

12. The method of claim 1 further comprising determining periods of time during which the object is being moved.

13. The method of claim 1, wherein the plurality of ambient atmospheric pressure measurements are obtained while the object is static.

14. The method of claim 13, wherein the comparison comprises determining a geo-location at which a variance between the plurality of ambient atmospheric pressure measurements and corresponding pressure data from the gridded atmospheric model is minimized.

15. The method of claim 1, wherein the plurality of ambient atmospheric pressure measurements are obtained while the object is in motion.

16. The method of claim 15 further comprising providing at least one of an initial or a final location of the object.

17. The method of claim 15 further comprising providing a maximum speed experienced by the object.

18. The method of claim 15, wherein the comparison comprises performing an iterative Bayesian procedure.

19. The method of claim 1, wherein the gridded atmospheric model is a model employed by a meteorological forecasting agency.

20. The method of claim 1, wherein the gridded atmospheric model is provided from a source selected from the group consisting of the Rapid Update Cycle Surface Assimilation System maintained by the National Oceanic and Atmospheric Association, and the Modern Era Retrospective—Analysis for Research and Applications maintained by the National Aeronautics and Space Administration.

21. The method of claim 1, wherein the object is attached, during the plurality of ambient atmospheric pressure measurements, to at least one of a shipping container, a manufacturing supply, or an individual.

22. A system for determining a geo-location of an object based at least in part on a plurality of ambient atmospheric pressure measurements obtained for the object, the system comprising:
- a processor that executes computer readable instructions; and
- computer memory that stores computer readable instructions that, when executed by the processor, cause an analysis module to:
  - compare the ambient atmospheric pressure measurements against a gridded atmospheric models and
  - determine, based at least in part on the comparison, the geo-location of the object.

23. The system of claim 22, wherein the analysis module determines the geo-location of the object without using an externally provided navigation signal.

24. The system of claim 23, wherein the analysis module determines the geo-location of the object without using a global positioning system signal.

25. The system of claim 22 further comprising a pressure sensor, associated with the object, that measures the ambient atmospheric pressure.

26. The system of claim 25 further comprising a second computer memory, associated with the object, that stores the plurality of ambient atmospheric pressure measurements.

27. The system of claim 26, wherein the pressure sensor measures the ambient atmospheric pressure as a function of time and the second computer memory stores the ambient atmospheric pressure measurements as a function of time.

28. The system of claim 25, wherein the pressure sensor obtains the plurality of ambient atmospheric pressure measurements while the object is static.

29. The system of claim 28, wherein the analysis module determines a geo-location at which a variance between the plurality of ambient atmospheric pressure measurements and corresponding pressure data from the gridded atmospheric model is minimized.

30. The system of claim 25, wherein the pressure sensor obtains the plurality of ambient atmospheric pressure measurements while the object is in motion.

31. The system of claim 30 further comprising an input module, in operative communication with the analysis module, that receives at least one of an initial or a final location of the object.

32. The system of claim 30 further comprising an input module, in operative communication with the analysis module, that receives a maximum speed experienced by the object.

33. The system of claim 30, wherein the analysis module executes an iterative Bayesian procedure.

34. The system of claim 22 further comprising an auxiliary sensor, associated with the object, that compensates for environmentally-induced errors in the pressure measurements.

35. The system of claim 34, wherein the auxiliary sensor comprises a temperature sensor that measures a temperature in a vicinity of the object.

36. The system of claim 34, wherein the auxiliary sensor comprises a humidity sensor that measures a humidity in a vicinity of the object.

37. The system of claim 34 further comprising a second computer memory, associated with the object, that stores a parameter measured by the auxiliary sensor.

38. The system of claim 37, wherein the auxiliary sensor measures the parameter as a function of time and the second computer memory stores the measured parameter as a function of time.

39. The system of claim 22 further comprising at least one of a vibration or an acceleration sensor, associated with the object, that determines periods of time during which the object is being moved.

40. The system of claim 22 further comprising the gridded atmospheric model.

41. The system of claim 40, wherein the gridded atmospheric model is a model employed by a meteorological forecasting agency.

42. The system of claim 40, wherein the gridded atmospheric model is provided from a source selected from the group consisting of the Rapid Update Cycle Surface Assimilation System maintained by the National Oceanic and Atmospheric Association, and the Modern Era Retrospective—Analysis for Research and Applications maintained by the National Aeronautics and Space Administration.

* * * * *

UNITED STATES PATENT AND TRADEMARK OFFICE
CERTIFICATE OF CORRECTION

PATENT NO. : 8,443,662 B2
APPLICATION NO. : 13/016055
DATED : May 21, 2013
INVENTOR(S) : Benjamin F. Lane et al.

It is certified that error appears in the above-identified patent and that said Letters Patent is hereby corrected as shown below:

In the Claims:

In Claim 22, column 23, line 22, please delete "models" and insert --model;--.

Signed and Sealed this
Sixteenth Day of July, 2013

Teresa Stanek Rea
*Acting Director of the United States Patent and Trademark Office*